United States Patent
Zimmerle

(10) Patent No.: US 7,561,272 B2
(45) Date of Patent: Jul. 14, 2009

(54) PRECISION CORRECTION OF REFLECTANCE MEASUREMENTS

(75) Inventor: Chris T. Zimmerle, Goshen, IN (US)

(73) Assignee: Siemens Healthcare Diagnostics Inc., Tarrytown, NY (US)

(*) Notice: Subject to any disclaimer, the term of this patent is extended or adjusted under 35 U.S.C. 154(b) by 355 days.

(21) Appl. No.: 10/595,241

(22) PCT Filed: Sep. 29, 2004

(86) PCT No.: PCT/US2004/032008

§ 371 (c)(1),
(2), (4) Date: Mar. 29, 2006

(87) PCT Pub. No.: WO2005/036144

PCT Pub. Date: Apr. 21, 2005

(65) Prior Publication Data
US 2007/0043519 A1    Feb. 22, 2007

Related U.S. Application Data

(60) Provisional application No. 60/508,830, filed on Oct. 3, 2003.

(51) Int. Cl.
G01N 21/55    (2006.01)

(52) U.S. Cl. .................................................. 356/445
(58) Field of Classification Search ................... 356/445
See application file for complete search history.

(56) References Cited

U.S. PATENT DOCUMENTS

| 4,160,646 A | 7/1979 | Furutani et al. |
| 6,267,722 B1 | 7/2001 | Desieno et al. |
| 2006/0139649 A1* | 6/2006 | Howard ....................... 356/445 |

FOREIGN PATENT DOCUMENTS

| EP | 0 816 849 A | 1/1998 |
| EP | 1411346 B1 | 4/2004 |
| WO | WO 01/73405 A | 10/2001 |
| WO | WO 03/056314 A | 7/2003 |

* cited by examiner

Primary Examiner—Kara E Geisel
(74) Attorney, Agent, or Firm—McDermott Will & Emery

(57) ABSTRACT

A system and method of correcting reflectance comprises determining a reflectance constant for a test product at a first wavelength for which reflectance does not substantially change with the presence of a test substance, with the test product loaded with the test substance, determining a reflectance at a second wavelength for which signal-to-noise ratio is maximized and determining a measured reflectance at the first wavelength, and determining a corrected reflectance as the product of the reflectance with a ratio of the reflectance constant to the measured reflectance.

30 Claims, 5 Drawing Sheets

PRECISION CORRECTION OF REFLECTANCE MEASUREMENTS

CROSS REFERENCES TO RELATED APPLICATIONS

This application claims the benefit of priority under 35 U.S.C. § 119(e) from co-pending, commonly owned U.S. provisional patent application Ser. No. 60/508,830, entitled Method For Increasing Precision Of Reflectance Measurements, filed Oct. 3, 2003.

FIELD OF INTEREST

The present inventive concepts relate to the field of reflectance-based systems, and more particularly to optimizing results and performance of reflectometers.

BACKGROUND

Reflectance-based instruments have long been in use in a variety of applications. One type of reflectance-based system is referred to as a "reflectometer", used to perform tests in certain medical and laboratory applications. In a typical form, a reflectometer includes one or more light sources configured to generate one or more light signals at given wavelengths. An object under test receives the signal and reflects a portion thereof—referred to as "reflectance". Reflectance is typically considered to be unit-less because it is defined as the ratio of the light actually leaving a sample to the amount that would leave if none were absorbed. In recent years, the National Institute of Standards and Technology (NIST) has defined reflectance in terms of this kind of mathematical model, rather than provide a physical reflectance standard. One or more detectors or sensors are oriented to receive the reflected signals. A processor analyzes the characteristics of the received reflected signals and produces a test result.

Such reflectometers are sometimes used for performing tests on a reagent test strip. In such a case, the test pads on the test strip may be incrementally tested to determine the presence of analytes in a liquid test sample absorbed into the test pads. Such systems may be used for performing urinalysis tests, as one example. That is, the level or presence of an analyte in a liquid test sample can be determined by causing a given test pad to absorb some of the liquid test sample, (e.g., a sample of urine) and then by reading associated reflectance values for the test pad with a reflectometer. Based on the reflectance characteristics of the signal reflected by the test pad, the reflectometer determines the presence or level of the analyte in a given test pad. As an example, a test pad changes color to indicate the level or presence of the analyte in response to absorption of urine from a urine sample. The characteristics of a reflected signal are a function of the make-up and color of the test pad and the wavelength of the light source. Consequently, a change in color of a test pad causes a corresponding change in the characteristics of the reflected signal.

Test strips are typically produced according to industry accepted formats. In the case of urinalysis reflectometers, test strips can come in formats having different lengths, such as, for example, 3.25 inch lengths or 4.25 inch lengths. Within each format, a test strip is defined according to its configuration, i.e., the number, types and order of test pads included on the test strip. Generally, each test strip configuration is uniquely identified. Implicit in a test strip identification and/or confirmation, therefore, is the test strip format and the test pad configuration. As will be appreciated by those skilled in the art, such test pads may include, for example, pH, ketone, nitrite, and glucose test pads. In order for the reflectometer to produce valid results, the test strip must be identified by format and configuration, so that the reflectometer has a proper context to evaluate the received reflected signals, or reflectance values derived therefrom. That is, a reflectometer needs to know that a received reflected signal is produced by, for example, a glucose test pad or a ketone test pad.

Reagent cassettes can also be tested using a reflectometer, in a manner very similar to that used for the test strip. Such reagent cassettes include a test region that provides visual indications of test results, similar to the test pads of the test strips. The test region can produce a series of lines that embody the test results.

There are numerous rapid test assays in the market utilizing immunochromatography devices. Most are limited to YES/NO answers because of their poor quantitation (i.e., poor ability to measure or estimate quantity with precision). To achieve a higher level of quantitation, reflectometers can be used to subjectively examine the colored bands formed on a test product. However, reflectance measurements in a reflectometer are prone to many sources of error because the positioning and height of the test strip or reagent cassette can greatly alter the amount of photons that reach the detector. Even slight differences in the height of a test product can alter the reflectance value obtained, thus becoming a source of error when measuring analyte concentration by reflectance measurements.

Some systems attempt to address these circumstances with a straightforward ratio-ing of wavelengths. The problem with just rationing the wavelengths is that there is great difficulty in associating meaning to such numbers and they do not lend themselves to processes or algorithms that utilize the related reflectance measurements for generating subsequent information or test results. For example, one process that uses reflectance values is the "K/S" transformation for linearizing reflectance measurements, which is given by the equation:

$$K/S(R) = (1-R)^2/(2*R) \quad (1)$$

Here, a ratio of wavelengths would not result in a reflectance value R useful in such an equation. Similar problems would be realized in other functions that rely on the use of R.

SUMMARY OF INVENTION

In accordance with one aspect of the present invention, provided is a method of correcting reflectance comprising determining a reflectance constant for a test product at a first wavelength for which reflectance does not substantially change with the presence of a test substance, with the test product loaded with the test substance, determining a reflectance at a second wavelength for which signal-to-noise ratio is maximized and determining a measured reflectance at the first wavelength, and determining a corrected reflectance as the product of the reflectance with a ratio of the reflectance constant to the measured reflectance.

In accordance with another aspect of the present invention, provided is a reflectance-based system including reflectance correction, the system comprising transmitters for transmitting signals at different wavelengths to a test product and detectors configured for detecting reflectance at the different wavelengths from the test product, a set of storage devices configured for storing reflectance values, a set of processors configured to execute a program configured to implement a method of correcting reflectance. The method comprises determining a reflectance constant for a test product at a first wavelength for which reflectance does not substantially change with the presence of a test substance, with the test product loaded with the test substance, determining a reflectance at a second wavelength for which signal-to-noise ratio is maximized and determining a measured reflectance at the first wavelength, and determining a corrected reflectance as the product of the reflectance with a ratio of the reflectance constant to the measured reflectance.

In accordance with yet another aspect of the present invention, provided is a computer program code embodying instructions for execution by at least one processor to perform a method for correcting reflectance in a reflectance-based device comprising transmitters for transmitting signals at different wavelengths to a test product and detectors configured for detecting reflectance at the different wavelengths from the test product, a set of storage devices configured for storing reflectance values. The method comprises determining a reflectance constant for a test product at a first wavelength for which reflectance does not substantially change with the presence of a test substance, with the test product loaded with the test substance, determining a reflectance at a second wavelength for which signal-to-noise ratio is maximized and determining a measured reflectance at the first wavelength, and determining a corrected reflectance as the product of the reflectance with a ratio of the reflectance constant to the measured reflectance.

In yet another aspect of the present invention provided is a reflectance-based system including reflectance correction, the system comprising transmitters for transmitting signals at different wavelengths to a test product and detectors configured for detecting reflectance at the different wavelengths from the test product, a set of storage devices configured for storing reflectance values, means for determining a reflectance constant for a test product at a first wavelength for which reflectance does not substantially change with the presence of a test substance, with the test product loaded with the test substance, means for determining a reflectance at a second wavelength for which signal-to-noise ratio is maximized and means for determining a measured reflectance at the first wavelength, and means for determining a corrected reflectance as the product of the reflectance with a ratio of the reflectance constant to the measured reflectance.

In accordance with any of the above aspects of the present invention, the test product may be a test strip or a reagent cassette and the test substance may be, for example, an analyte.

BRIEF DESCRIPTION OF THE DRAWINGS

The drawing figures depict preferred embodiments by way of example, not by way of limitations. In the figures, like reference numerals refer to the same or similar elements.

DETAILED DESCRIPTION OF PREFERRED EMBODIMENT

In accordance with the present invention, provided is a method that allows the benefit of wavelength ratio-ing and ability to perform subsequent transformations using corrected reflectance measurements. In the preferred embodiment, improved intra-assay precision results are achieved by correcting reflectance readings of a colored particle or substance by using a ratio of a predetermined reflectance constant to the actual measured value at a wavelength removed from the colored particle and substance and unaltered by changes in concentration of that particle or substance.

Representative Reflectance-Based Instrument

Figure 1:
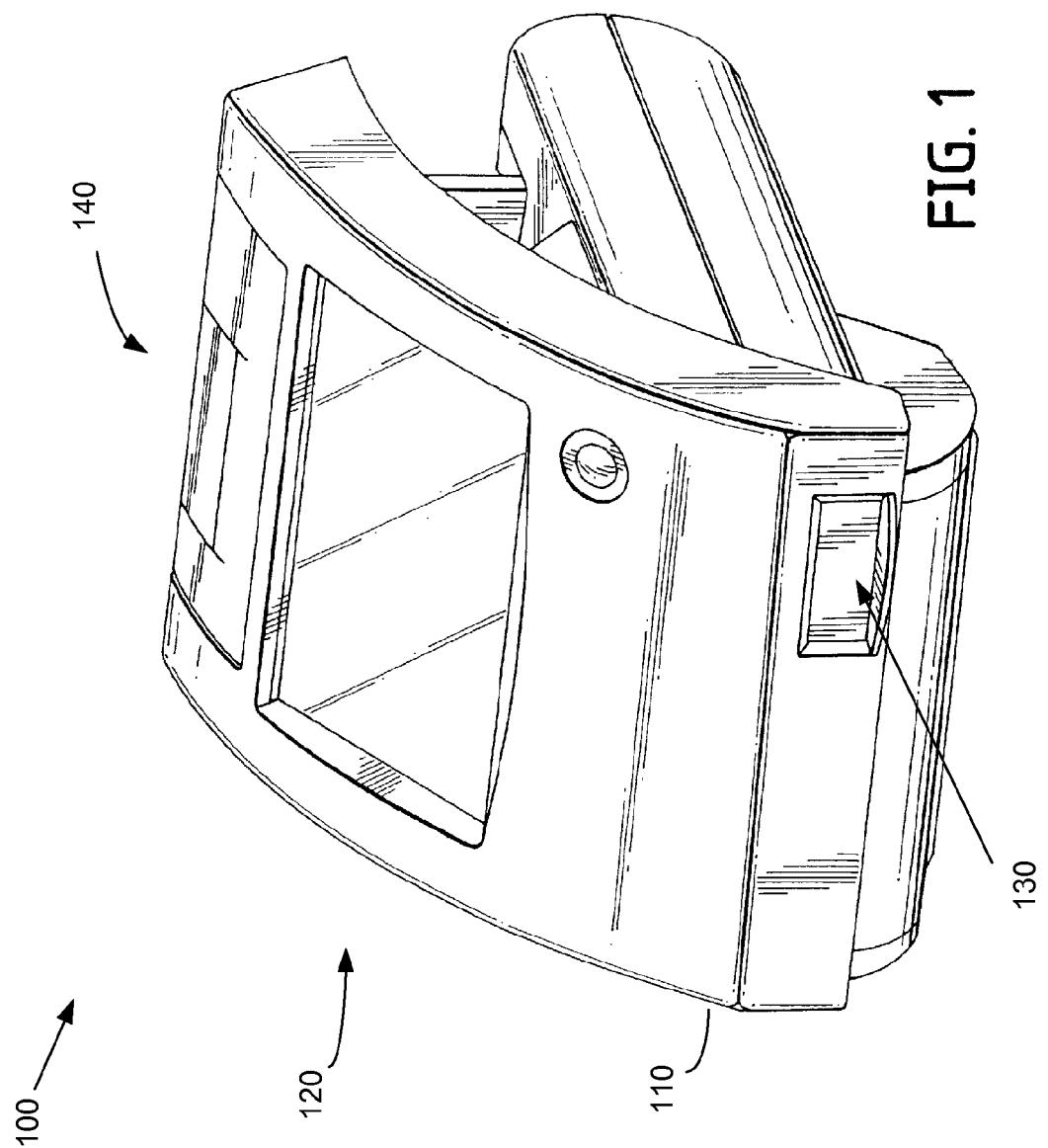
FIG. 1 is a perspective of a reflectometer that could include the correction provided by the present invention.

FIG. 1 provides a perspective view of an embodiment of a reflectometer 100, as one example of a reflectance-based instrument, that may include functionality that implements the reflectance correction of the present invention. As will be appreciated by those skilled in the art, the present invention could be implemented in other reflectometers or reflectance-based instruments, so is not restricted to embodiments provided herein. Reflectometer 100 provides an input and output device in the form of a touch screen 120. An output port 140 may be provided as a means for printing a report (e.g., test or diagnostic report) to an operator or user of reflectometer 100. As will also be appreciated by those skilled in the art, other forms of input and output mechanisms may be used. For example, reflectometer 100 may be configured to couple, by wired or wireless means, to a personal computer, handheld computer, network, monitor, printer, audio/visual system or the like. A housing 110 houses the touch screen 120, as well as a variety of internal functional elements. An input port 130 is provided to facilitate insertion of one or more test strips or reagent cassettes (collectively, "test product(s)") via a carriage.

Figure 2:
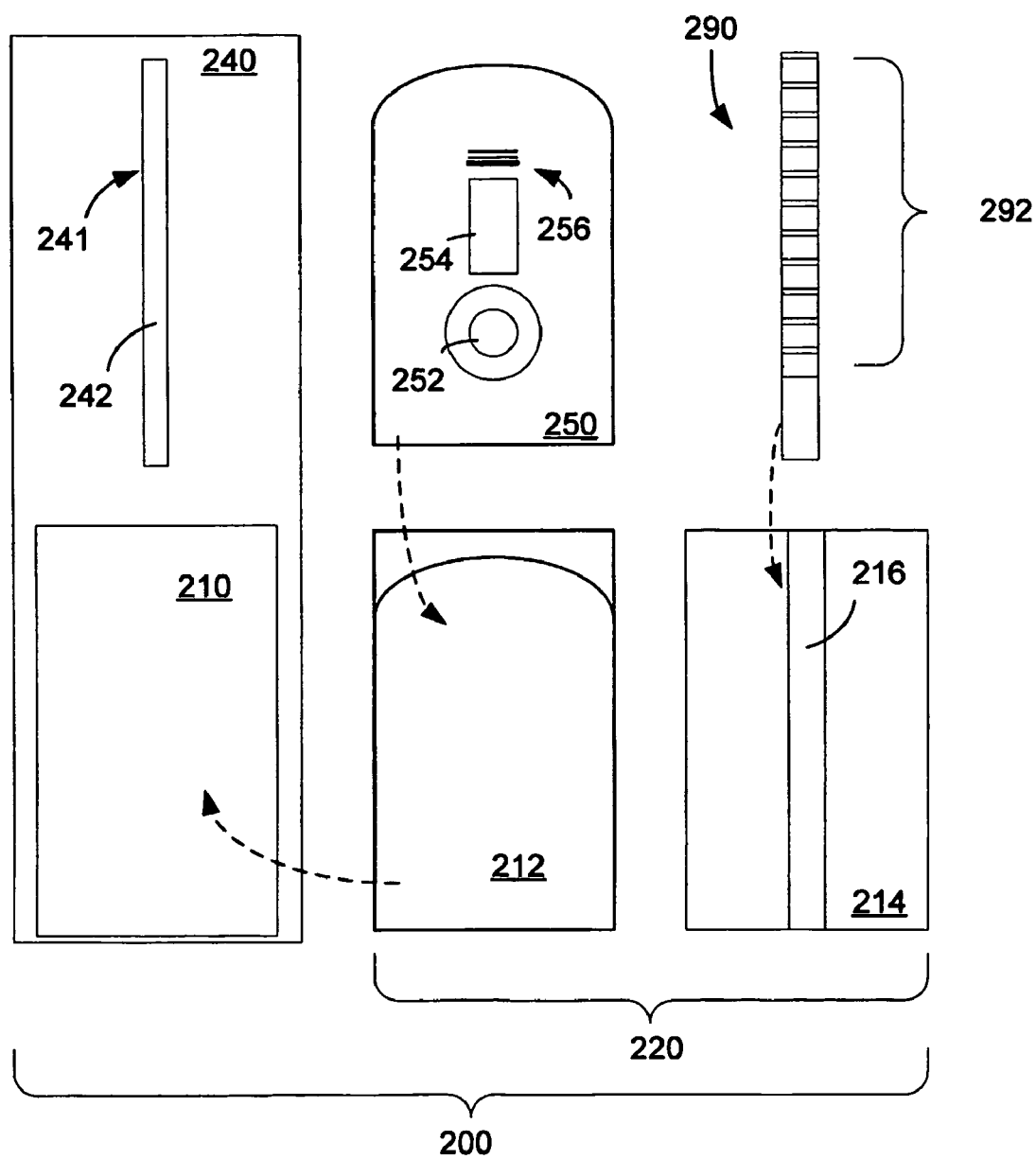
FIG. 2 are prior art views of a carriage used with the spectrometer of FIG. 1, including a view of a insert used with the carriage for accommodating various test strips.

Referring to FIG. 2, a collection of test product insertion components 200 for use with reflectometer 100 is shown. A carriage 240 is configured for insertion in input port 130 of the reflectometer 100, with a test product. Carriage 240 includes an insert region 210 within which a test product insert 220 configured to hold a test product (e.g., a reagent test strip 290 or cassette 250) may be placed. In the preferred form, insert 220 includes a first side 214 configured to hold the reagent test strip 290 within a slot 216. Representative test strip 290 includes a plurality of test pads 292, the configuration of which depends on the particular test strip type. Once test strip 290 is positioned within slot 216, the insert 220 may be loaded into carriage 240 with side 214 available for testing. Carriage 240 may be configured to accommodate a test strip 290 of any of a variety of lengths, such as test strips of the 3.25" and 4.25" length formats, as examples.

A region of interest to be tested may include one or more of test pads 292. In order for the test pads 292 to be tested, those pads must be disposed to receive light from the LEDs and to reflect light for detection by light detectors, as described with respect to FIG. 3A and FIG. 3B below. Accordingly, in the embodiment of FIG. 2, test strip 290 is disposed within carriage 240 such that the test strip pads 292 are visible to such components.

Insert 220 may optionally include a second side 212 configured to accept reagent cassette 250. Such reagent cassettes are known in the art. For instance, reagent cassette 250 may be a disposable, single-use hCG amino cassette for performing a pregnancy test. The reagent cassette 250, as with the test strip 290, includes a region of interest that may include a test area defined by a window 254 and also include identification markings, such as bar codes 256. The reagent test area is viewable and capable of being tested when the carriage is loaded into reflectometer 100.

The reagent cassette 250 has an opening or well 252 into which a test substance, e.g., a body fluid sample such as urine, is deposited. The fluid sample propagates to the test area defined by window 254. The reagent cassette test area comprises a test line area, reference line area and control line area, as is known in the art. Test results can take the form of one or more lines displayed in these areas in response to the introduction (or loading) of the test substance. With introduction of a fluid sample, the reagent cassette test area may change color, for example, at least one colored stripe may appear in window 254.

As an example, the various components of FIG. 2 may take the form of those more fully described in co-owned and co-pending U.S. patent application Ser. No. 10/821,441, entitled TRAY ASSEMBLY FOR OPTICAL INSPECTION APPARATUS, filed Apr. 9, 2004.

Figure 3A:
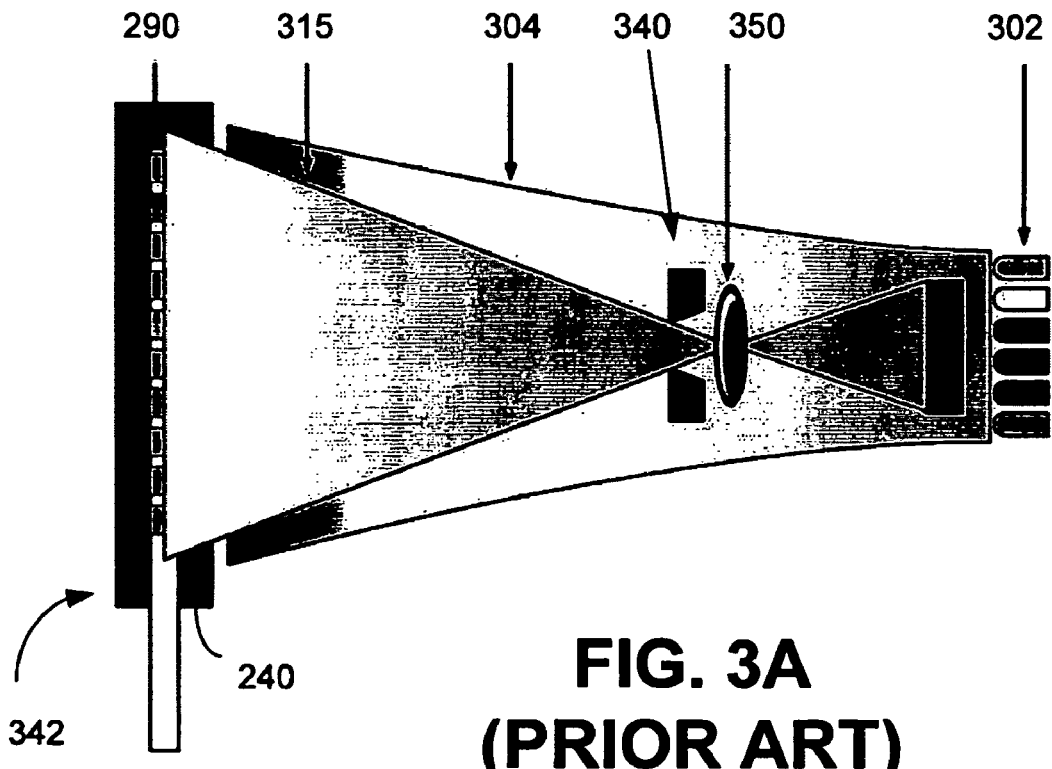
FIG. 3A and FIG. 3B are prior art diagrams depicting the arrangement of functional elements within the reflectometer of FIG. 1.
Figure 3B:
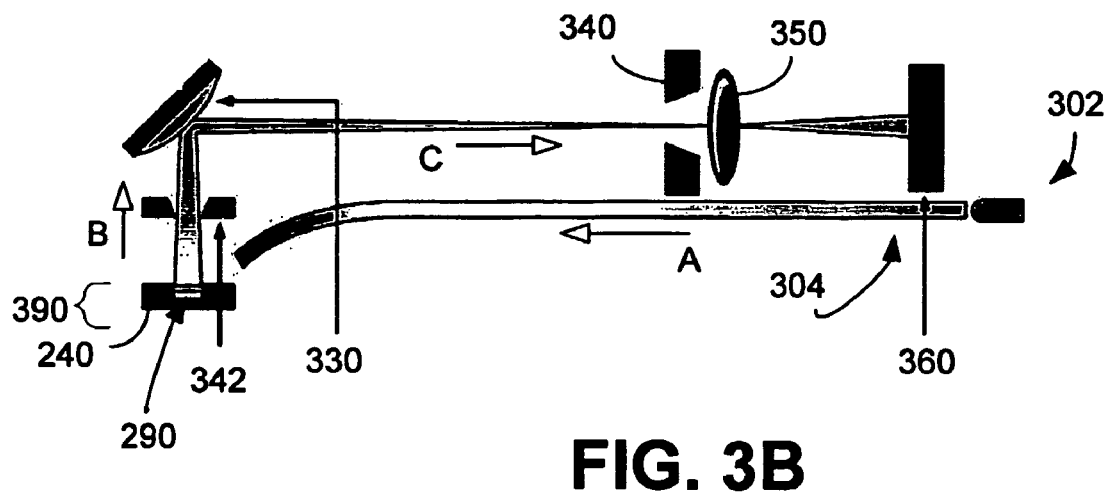

FIGS. 3A and 3B show two different views of an embodiment of various functional elements that may be used for performing reflectance-based testing of a test product within reflectometer 100. A top view is shown in FIG. 3A and a side view is shown in FIG. 3B. As is shown in each of the figures, test signals are provided by transmitters 302. In this form, transmitters 302 are LEDs, preferably six, as shown in FIG. 3A, each of which transmits a different signal having a unique wavelength.

In this embodiment, the signals transmitted by the LEDs are:
1) LED 1: blue light at a center wavelength of about 470 nanometers (nm),
2) LED 2: green light at a center wavelength of about 525 nm,
3) LED 3: green light at a center wavelength of about 565 nm,
4) LED 4: red light at a center wavelength of about 625 nm,
5) LED 5: red light at a center wavelength of about 660 nm, and
6) LED 6: infrared (IR) signal at a center wavelength of about 845 nm.

Test signals from LEDs 302 are transmitted through a guide 304 in the direction of arrow A. The test signals from guide 304 impinge on test product 390 (e.g., reagent cassette 250 or test strip 290 housed within carriage 240) at an angle of about 45°, in the illustrative embodiment. Light reflected from the test product 390 in the direction of arrow B passes through aperture 342, after which it impinges on convex mirror 330 (not shown in FIG. 3A), which redirects and focuses the reflected signals in the direction of arrow C. In this arrangement, due to the orientation of mirror 330, the path of the reflected signals takes about a 90° turn after leaving the test product 390. The reflected signals propagating in the direction of arrow C pass through aperture 340 and converge at aspheric lens 350. Aspheric lens 350 diverges the reflected signals and the diverged reflected signals continue to propagate in the direction of arrow C. The reflected signals impinge on detector 360. As will be appreciated by those skilled in the art, the shapes and arrangement of mirrors and lenses need not specifically conform to or be limited to those shown in the illustrative embodiment of FIGS. 3A and 3B.

Upon receipt of the reflected signals, detector 360 translates those signals into an image comprised of data representing reflectance values associated with the test product 390, and tests results are derived therefrom. In this embodiment, detector 360 is a charge coupled device (CCD) comprised of a matrix of 2048 pixels configured to receive the reflected signals. Data from the reflected signals are recorded pixel-by-pixel as the reflectance values. Pixel data are grouped and associated with portions of the test product 390. As a result, reflectance values for test portions of the test product 390 are stored.

Reflectance Correction

The present invention achieves increased precision in the reflectance measurements of a reflectance-based device, such as the reflectometer 100 described above in FIGS. 1-3B. In such a reflectometer, test results may be determined by processing measurements of the reflectance of test areas comprised of particles or substances that become colored in response to the introduction of a test substance to the test product, such as an analyte. Differences in parameters having no relationship to the concentration of the analyte can causes differences in the reflectance values, and thus errors in the test results. The correction provided by the present invention allows for better calibration of such reflectometers, and thus better results. For example, a reagent cassette may include a white band having particles that respond to the analyte by turning red and blue. In such a case, as an example, the red particles may form a red line in the presence of the analyte. In a test strip, a certain area may be similarly configured.

In accordance with the present invention, reflectance readings of the colored particle or substance are corrected using a ratio of a known reflectance constant ($R_{\lambda\text{-}const}$), to a measured reflectance value ($R_{\lambda\text{-}meas}$), both determined at the same wavelength ($\lambda$). The wavelength $\lambda$ is chosen to be a wavelength for which reflectance is substantially unaltered by the introduction or concentration of the analyte to be tested. This wavelength would typically be removed spectrally from that used to obtain test results for the colored particle or substance. Choosing the wavelength $\lambda$ in this way ensures that any differences between the known reflectance constant $R_{\lambda\text{-}const}$ and the measured reflectance value $R_{\lambda\text{-}meas}$ will not be a function of the analyte, but rather a function of one or more other error causing factors previously discussed.

Figure 4A:
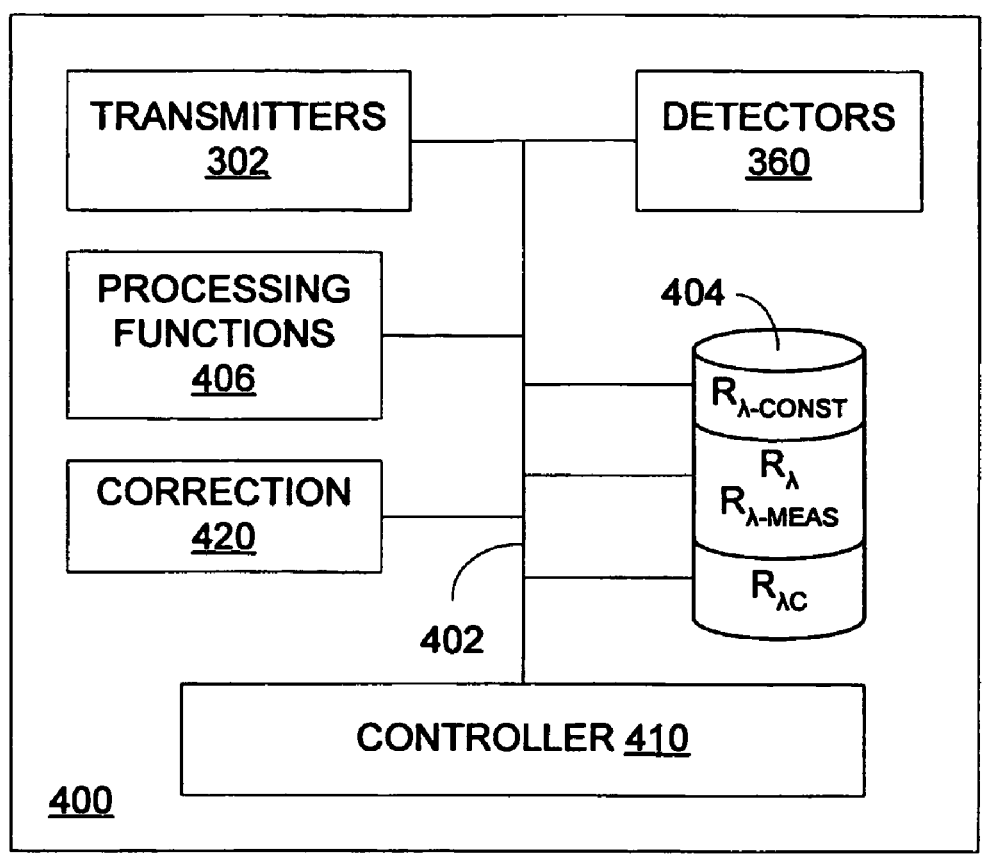
FIG. 4A is a block diagram of a set of modules that may be used to implement the present invention.

FIG. 4A is block diagram depicting an illustrative embodiment of functional components or modules 400 of a reflectometer implementing reflectance correction in accordance with the present invention. One or more buses 402 may be used to facilitate communications among the various modules, as is generally known in the art. As was shown in FIG. 3A and FIG. 3B, transmitters 302 generate signals that reflect off of a test product and are then detected by detectors 360. The detected reflectance values may be stored within one or more storage devices, depicted as a set of storage devices 404 in FIG. 4A. One or more modules may be provided for performing various known processing functions, such as those used to determine test results, depicted generally as processing functions 406. One specific example of such a function is the K/S function used to linearize reflectance results. A controller 410 may be used to generally manage the various functional modules, the flow of data and instructions therebetween and the flow of data to and from the set of storage devices 404.

A correction module 420 may also be included in the functional modules 400 of FIG. 4A. In the illustrative embodiment, correction module 420 implements a method for correcting reflectance values in accordance with the present invention. A method in accordance with the embodiment is provided in the flowchart 450 of FIG. 4B. Using such a method, intra-instrument error caused by inaccurate reflectance measurements is reduced. The method implements reflectance correction according to the following equation:

$$R_{\lambda'c} = [R_{\lambda\text{-}const}/R_{\lambda\text{-}meas}] * R_{\lambda'} \qquad (2)$$

where $R_{\lambda'c}$ is the corrected reflectance value for a given wavelength or broadband filter.

$R_{\lambda\text{-}const}$ is the corrected reflectance value constant for the wavelength $\lambda$—which is a wavelength unresponsive to analyte concentration.

$R_{\lambda'}$ is the observed reflectance value measured using the wavelength with the highest signal to noise, $\lambda'$.

$R_{\lambda\text{-}meas}$ is the observed reflectance value $\lambda$.

Returning to step 4B, in step 452 the wavelength $\lambda$ is determined for which reflectance is relatively unaltered by the concentration of the analyte, i.e., has substantially no reflectance due to binding chemistry with the test product. Thus, any changes in the reflectance are presumed to be due to variations in the membrane, instrument, or test product orientation (e.g., test strip height), and not as a function of the concentration of an analyte. Variations in reflectance caused by these factors are often observed at all LED wavelengths, so regardless of the wavelength, reflectance correction is appropriate. In the illustrative embodiment, the source is an IR LED source having a wavelength of about $\lambda$=850 nm, for which the reflectance of the white band of the test product is substantially unaltered, regardless of the introduction or concentration of an analyte. As an example, for gold sol labeled conjugate this IR wavelength is appropriate because little or no IR reflectance is associated with this label. The reference wavelength chosen can be a wavelength other than the IR, so long has it does not exhibit any substantial signal changes associated with increasing analyte concentration.

$R_{\lambda\text{-}const}$ is determined in step 454, and may be referred to as the wavelength constant. In the illustrative form, this value is determined by averaging numerous runs and obtaining the average reflectance over those runs for the wavelength $\lambda$. Thus, the wavelength constant may be experimentally determined as an average reflectance across several measurements. It could also be determined over several reflectometers. Otherwise, the wavelength constant could be determined using predictive techniques or, in some cases, the wavelength constant could be based on information generally known. For wet nitrocellulose membrane affixed to a polystyrene test strip, as an example, $R_{\lambda\text{-}const}$ may be assigned the value of 75%. By using this known value for the IR, variations at all of the measured wavelengths can be corrected by using the ratio shown in Equation 2. Raw reflectance values used in any algorithm are adjusted in this manner, before they are incorporated into any specific algorithm or function 406 (also see step 464 of FIG. 4B).

$R_{\lambda'}$ is determined in step 456, as the reflectance value measured using the wavelength with the highest signal to noise (SNR), here represented by $\lambda'$. Choosing the wavelength where SNR is the highest is preferred because doing so allows the noise to be most easily distinguished from the actual reflected signal. Thus, such a wavelength allows for the best calibration of the reflectometer using the correction of the present invention. In this embodiment, $\lambda'$ is chosen to be about 525 nm, which is the wavelength for which the SNR for reflectance of the red particles embedded within the white band of the test product is maximized. Alternatively, a wavelength could have been chosen that maximized reflectance of the blue particles. In this embodiment, $R_{\lambda'c}$ is determined by sending a pulse scan from an LED at wavelength of $\lambda'$=525 nm.

$R_{\lambda\text{-}meas}$ is determined in step 458 as the reflectance observed at the wavelength $\lambda$, which is the wavelength for which $R_{\lambda\text{-}const}$ was determined. It is, therefore, the wavelength that demonstrates no significant signal changes due to increased analyte concentration. Since $\lambda$=850 nm in this embodiment, $R_{\lambda\text{-}meas}$ is the reflectance determined through the IR filter of the reflectometer when the IR source transmits a signal at a wavelength of about 850 nm. In this embodiment, $R_{\lambda\text{-}meas}$ is determined by sending a pulse scan of IR at a wavelength of 850 nm. This pulse scan is sent immediately after the $\lambda'$=525 nm pulse scan, or at least close enough in time so that there is no significant change in conditions relative to the conditions at the time of the $\lambda'$=525 nm pulse scan. If conditions between scans are allowed to change significantly, Equation 2 above may not continue to be valid for a given calculation.

$R_{\lambda\text{-}const}$ and $R_{\lambda\text{-}meas}$ can both be stored in the set of storage devices 404 of FIG. 4A; the measured value $R_{\lambda'}$ can also be stored in this set of storage devices. With $R_{\lambda\text{-}const}$ and $R_{\lambda\text{-}meas}$ known, a ratio can be determined as is shown in Equation (2) above, i.e., as $[R_{\lambda\text{-}const}/R_{\lambda\text{-}meas}]$. From these known values, the corrected reflectance $R_{\lambda c}$ can be determined for the wavelength $\lambda'$ by correction module 420 of FIG. 4A, and as is shown in step 460 of FIG. 4B.

Figure 4B:
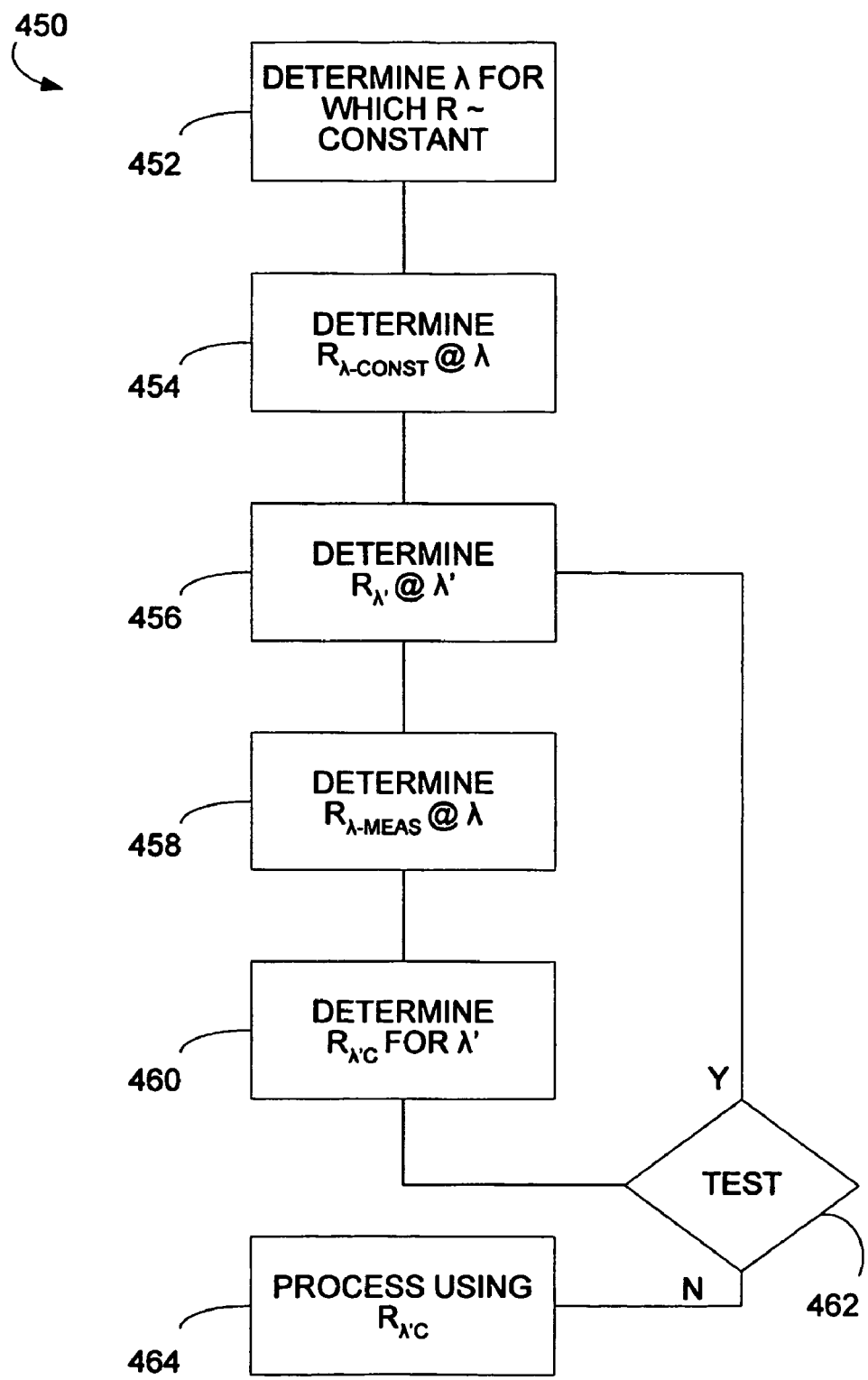
FIG. 4B is a flowchart of a method that may be implemented by the modules of FIG. 4A.

In FIG. 4B, decision box 462 indicates that the steps 456 through 460 can be carried out numerous times during operation—as a continuous or periodic calibration. That is, if the answer to the question in box 462 is yes, then the process could continue to box 456. If the answer is no, then the process could continue to step 464 where $R_{\lambda'c}$ could be used by the processing functions module 406. The corrected reflectance $R_{\lambda'c}$ could then, for example, be used in K/S linearization algorithm depicted by the following equation:

$$K/S(R_c) = (1-R_c)^2/(2R_c) \qquad (3)$$

In some embodiments, the test box 462 could be omitted and the process would go from box 460 directly to box 464.

To illustrate an example of results using the above aspects of the present invention, a 7 sample, 3 replicate run of a rapid PSA (Prostate specific antigen) immunochromatography strip gave the reflectance's before and after the correction shown below in Table 1. Here the Capture Band is a monoclonal anti-PSA striped onto the nitrocellulose and the Collection Band is rabbit anti-goat antibody. The signal was generated by a gold sol particle coated with goat anti-PSA.

TABLE 1

|  | Raw % R SD (pooled from all levels) | Corrected % R SD (pooled from all levels) | Fold reduction in % R SD |
| --- | --- | --- | --- |
| Capture Band | 2.0 | 1.14 | 1.75 |
| Collection Band | 1.85 | 0.67 | 2.76 |

Above, the standard deviation (SD) was relatively high in the uncorrected (or "raw") data (e.g., 2.0 and 1.85), but was much better in the corrected data (e.g., 1.14 and 0.67). Here the data is "pooled" data, rather than data for an individual test. The "Fold reduction in % R SD" is determined by dividing the Raw % R SD by the Corrected % R SD. Obviously, fold reductions>1 indicates improvements in precision.

Since IR correction removes error between replicate readings, it is also important in increasing the signal to noise ratio (SNR), as shown in the example in Table 2 below, where the sample size was N=12. In this example, comparing the SD for Raw versus the SD for IR-correction, the imprecision, the imprecision, given by the SD, was reduced by as much as 75%, or more, in some cases.

TABLE 2

| [DPD] | First Capture Zone | | | | First Collection Zone | | | |
|---|---|---|---|---|---|---|---|---|
| | Raw | | IR correction | | Raw | | IR correction | |
| | % R | SD | % R | SD | % R | SD | % R | SD |
| 0 | 63.1 | 1.1 | 62.6 | 0.5 | 76.9 | 2 | 73.7 | 0.5 |
| 10 | 62.5 | 1.5 | 63.6 | 0.3 | 75.2 | 2.3 | 73.7 | 0.7 |
| 25 | 67.2 | 2.3 | 66 | 0.5 | 70 | 2.5 | 67.5 | 0.5 |
| 75. | 67.1 | 1.7 | 67.9 | 0.6 | 60.2 | 2.1 | 60.4 | 0.6 |
| 150 | 71.1 | 3.2 | 71.1 | 0.7 | 60 | 2.8 | 60.2 | 0.8 |
| 250 | 72.7 | 2.4 | 71.8 | 0.4 | 61.4 | 2.1 | 60.5 | 0.6 |
| AVG | | 2.0 | | 0.5 | | 2.3 | | 0.6 |

While the foregoing has described what are considered to be the best mode and/or other preferred embodiments, it is understood that various modifications may be made therein and that the invention or inventions may be implemented in various forms and embodiments, and that they may be applied in numerous applications, only some of which have been described herein. As used herein, the terms "includes" and "including" mean wihtout limitation. It is intended by the following claims to claim any and all modifications and variations that fall within the true scope of the inventive concepts.

What is claimed is:

1. A method of correcting reflectance values measured for different test products within a reflectance-based instrument, the method comprising the steps of:
   A. for a first test product analyzed by the reflectance based instrument, determining a reflectance constant at a first wavelength for which reflectance does not substantially change with the presence of a test substance;
   B. with the test product loaded with the test substance, determining a maximized SNR reflectance at a second wavelength for which signal-to-noise ratio is maximized and determining a measured reflectance at the first wavelength; and
   C. determining a corrected reflectance as the product of the maximized SNR reflectance with a ratio of the reflectance constant to the measured reflectance.

2. The method of claim 1 wherein the test substance is an analyte.

3. The method of claim 1 wherein the test product is a test strip comprising a plurality of test pads.

4. The method of claim 1 wherein the test product is a reagent cassette.

5. The method of claim 1 wherein the measured reflectance is determined with a pulse scan at the second wavelength.

6. The method of claim 1 wherein the reflectance constant is determined with a pulse scan at the first wavelength.

7. The method of claim 1 wherein the reflectance constant is determined before conditions relative to a concentration of the test substance substantially changes from the time the measured reflectance was determined.

8. A reflectance-based system including reflectance correction for different test products within a reflectance-based instrument, the system comprising:
   A. transmitters for transmitting signals at different wavelengths to a test product and detectors configured for detecting reflectance at the different wavelengths from the test product;
   B. a set of storage devices configured for storing reflectance values;
   C. a set of processors configured to execute a program configured to implement a method of correcting reflectance comprising the steps of:
      i) determining a reflectance constant for the test product at a first wavelength for which reflectance does not substantially change with the presence of a test substance;
      ii) with the test product loaded with the test substance, determining a maximized SNR reflectance at a second wavelength for which signal-to-noise ratio is maximized and determining a measured reflectance at the first wavelength; and
      iii) determining a corrected reflectance as the product of the maximized SNR reflectance with a ratio of the reflectance constant to the measured reflectance.

9. The system of claim 8 wherein the test substance is an analyte.

10. The system of claim 8 wherein the test product is a test strip comprising a plurality of test pads.

11. The system of claim 8 wherein the test product is a reagent cassette.

12. The system of claim 8 wherein the measured reflectance is determined with a pulse scan at the second wavelength.

13. The system of claim 8 wherein the reflectance constant is determined with a pulse scan at the first wavelength.

14. The system of claim 8 wherein the reflectance constant is determined before conditions relative to a concentration of the test substance substantially changes from the time the measured reflectance was determined.

15. A computer readable program product embodying instructions for execution by at least one processor to perform a method for correcting reflectance values measured for different test products in a reflectance-based device comprising transmitters for transmitting signals at different wavelengths to a test product and detectors configured for detecting reflectance at the different wavelengths from the test product, and a set of storage devices configured for storing reflectance values, the method comprising:
   A. determining a reflectance constant for a test product at a first wavelength for which reflectance does not substantially change with the presence of a test substance;
   B. with the test product loaded with the test substance, determining a maximized SNR reflectance at a second wavelength for which signal-to-noise ratio is maximized and determining a measured reflectance at the first wavelength; and
   C. determining a corrected reflectance as the product of the maximized SNR reflectance with a ratio of the reflectance constant to the measured reflectance.

16. The computer program product of claim 15 wherein the test substance is an analyte.

17. The computer program product of claim 15 wherein the test product is a test strip comprising a plurality of test pads.

18. The computer program product of claim 15 wherein the test product is a reagent cassette.

19. A reflectance-based system including reflectance correction for different test products, the system comprising:
   A. transmitters for transmitting signals at different wavelengths to a test product and detectors configured for detecting reflectance at the different wavelengths from the test product;
   B. a set of storage devices configured for storing reflectance values;

C. means for determining a reflectance constant for the test product at a first wavelength for which reflectance does not substantially change with the presence of a test substance;

D. with the test product loaded with the test substance, means for determining a maximized SNR reflectance at a second wavelength for which signal-to-noise ratio is maximized and means for determining a measured reflectance at the first wavelength; and E. means for determining a corrected reflectance as the product of the maximized SNR reflectance with a ratio of the reflectance constant to the measured reflectance.

20. The system of claim 19 wherein the test substance is an analyte.

21. The system of claim 19 wherein the test product is a test strip comprising a plurality of test pads.

22. The system of claim 19 wherein the test product is a reagent cassette.

23. The method of claim 1 further comprising repeating steps A through C for a second test product.

24. The method of claim 1 wherein step C, determining a corrected reflectance, comprises determining a corrected reflectance value according to the following equation:

$$R_{\lambda'c} = [R_{\lambda\text{-}const}/R_{\lambda\text{-}meas}] * R_{\lambda'},$$

where $R_{\lambda'c}$ is the corrected reflectance value for a given wavelength or broadband filter, $R_{\lambda\text{-}const}$ is the corrected reflectance value constant for the wavelength $\lambda$, wherein $\lambda$ is a wavelength unresponsive to analyte concentration, $R_{\lambda'}$ is the maximized SNR reflectance value measured using the wavelength with the highest signal to noise, $\lambda'$, and $R_{\lambda\text{-}meas}$ is the measured reflectance value at wavelength $\lambda$.

25. The system of claim 8 wherein the set of processors are configured to execute steps (i)-(iii) for a second test product.

26. The system of claim 8 wherein the set of processors are configured to execute determining a corrected reflectance value according to the following equation:

$$R_{\lambda'c} = [R_{\lambda\text{-}const}/R_{\lambda\text{-}meas}] * R_{\lambda'},$$

where $R_{\lambda'c}$ is the corrected reflectance value for a given wavelength or broadband filter, $R_{\lambda\text{-}const}$ is the corrected reflectance value constant for the wavelength $\lambda$, wherein $\lambda$ is a wavelength unresponsive to analyte concentration, $R_{\lambda'}$ is the maximized SNR reflectance value measured using the wavelength with the highest signal to noise, $\lambda'$, and $R_{\lambda\text{-}meas}$ is the measured reflectance value at wavelength $\lambda$.

27. The program product of claim 15 further comprising instructions for repeating steps A through C for a second test product.

28. The program product of claim 15 wherein instructions for step C, determining a corrected reflectance, comprise instructions for determining a corrected reflectance value according to the following equation:

$$R_{80'c} = [R_{\lambda\text{-}cons}/R_{\lambda\text{-}meas}] * R_{\lambda'},$$

where $R_{\lambda'c}$ is the corrected reflectance value for a given wavelength or broadband filter, $R_{\lambda\text{-}const}$ is the corrected reflectance value constant for the wavelength $\lambda$, wherein $\lambda$ is a wavelength unresponsive to analyte concentration, $R_{\lambda'}$ is the maximized SNR reflectance value measured using the wavelength with the highest signal to noise, $\lambda'$, and $R_{\lambda\text{-}meas}$ is the measured reflectance value at wavelength $\lambda$.

29. The system of claim 19 wherein the transmitters and receivers are configured for use with a second test product.

30. The system of claim 19, wherein the means for determining a corrected reflectance is configured to determine the corrected reflectance value according to the following equation:

$$R_{80'c} = [R_{\lambda\text{-}cons}/R_{\lambda\text{-}meas}] * R_{\lambda'},$$

where $R_{\lambda'c}$ is the corrected reflectance value for a given wavelength or broadband filter, $R_{\lambda\text{-}const}$ is the corrected reflectance value constant for the wavelength $\lambda$, wherein $\lambda$ is a wavelength unresponsive to analyte concentration, $R_{\lambda'}$ is the maximized SNR reflectance value measured using the wavelength with the highest signal to noise, $\lambda'$, and $R_{\lambda\text{-}meas}$ is the measured reflectance value at wavelength $\lambda$.

\* \* \* \* \*